United States Patent
Frangi et al.

(12)

(10) Patent No.: US 6,342,044 B1
(45) Date of Patent: Jan. 29, 2002

(54) ELASTIC WAISTBAND WITH TRANSVERSE STIFFENERS AND TAUTNESS ADJUSTING LACINGS

(75) Inventors: Giampietro Frangi; Gianluigi Frangi, both of Varese (IT)

(73) Assignee: Pavis Varese S.R.L., Varese (IT)

( * ) Notice: Subject to any disclaimer, the term of this patent is extended or adjusted under 35 U.S.C. 154(b) by 0 days.

(21) Appl. No.: 09/486,049

(22) PCT Filed: Jun. 25, 1998

(86) PCT No.: PCT/IT98/00176

§ 371 Date: Feb. 22, 2000

§ 102(e) Date: Feb. 22, 2000

(87) PCT Pub. No.: WO99/66869

PCT Pub. Date: Dec. 29, 1999

(51) Int. Cl.[7] ................................................. A61F 5/00
(52) U.S. Cl. .............................. 602/19; 602/21; 602/26; 602/60; 602/62; 602/63; 602/65; 602/75
(58) Field of Search ............................ 602/19, 13, 14, 602/21, 26, 60, 62, 63, 65, 74, 75, 76, 79; 2/455, 456, 24, 170; 428/99, 224, 230, 231, 252, 253, 258, 259

(56) References Cited

U.S. PATENT DOCUMENTS

| 2,554,337 A | 5/1951 | Lampert ....................... 128/96 |
| 3,927,665 A | 12/1975 | Wax ............................. 128/78 |
| 5,560,046 A | 10/1996 | Iwamasa et al. ............... 2/328 |

FOREIGN PATENT DOCUMENTS

| DE | 28 37 620 A1 | 3/1980 |
| GB | 2 243 787 A | 11/1991 |
| WO | WO 92/19201 | 11/1992 |

*Primary Examiner*—Michael A. Brown
*Assistant Examiner*—Lalita M Hamilton
(74) *Attorney, Agent, or Firm*—Connolly Bove Lodge & Hutz

(57) ABSTRACT

An elastic waistband comprises at least a main portion (A) made of an elastic fabric, a first end portion (B) in the form of two triangle-shaped tails (B1, B2) joined together to said main portion (A) and having at their free ends with Velcro® fasteners (V1, V2) and a second end portion (C) having anchoring felt pads (P) for the Velcro® Fasteners (V1, V2). The elastic main portion (A) is composed of a first central portion (A1) of a fabric (1) of greater elasticity than the elasticity of a fabric (2) of two side portions (A2, A3), joined together along transverse sewing lines (A1–2), A1–3). Transverse stiffening inserts (S1, S2, S3, S4) are disposed in correspondence of the transverse sewing lines joining together the first central portion (A1), the side portions (A2, A3) and the first and second end portions (B, C). Secondary elastic tautness adjustment means, runs over the exterior of the elastic portions (A1, A2, A3) and of the inserts and are in the form of a plurality of pairs (4, 5, 6) of interlaced multistrip bands, spacingly arranged along the height of the waistband, each multistrip band being composed of a plurality of parallel textile strips (4a–4b, 5a–5b, 6a–6b) having their free ends joined together to a piece of Velcro® fastener material (V4, V5, V6) and the other ends permanently sew along the farthest one from said free ends of said transverse sewing lines (A1-2, A1-3) joining the first central portion (A1) of elastic fabric (1) to a respective side portion (A2, A3) of stiffer elastic fabric (2). The Velcro® fasteners (V4, V5, V6) of the opposite free ends of each pair of interlaced bands may be pulled apart and anchored on the outer surface of said first (B) and second (C) end portions, respectively for adjusting the relative stretching of said elastic portions (A1, A2, A3) and block said stiffeners (S1, S2, S3, S4).

2 Claims, 4 Drawing Sheets

ELASTIC WAISTBAND WITH TRANSVERSE STIFFENERS AND TAUTNESS ADJUSTING LACINGS

FIELD OF THE INVENTION

The present invention relates to garments and sanitary protections which can be tightly worn on a body part or articulation to be protected or aided in its mechanical action and more particularly to an elastic waistband with transverse stiffeners and tautness adjustment lacings.

BACKGROUND OF THE INVENTION

In making elastic sanitary implements for aiding the mechanical action of articulations, in order to recover their full functionality after injuries or as a form of prevention in performing sporting activities involving relatively high stresses on muscles and/or articulations, it is necessary to ensure, besides the comfort of use, a good adjustability of the elastic tautness.

The conventional tubular elastic sanitary protections are not capable of satisfying the adjustability requirement and can be produced only in a series of relatively standardized sizes.

For uses absolutely requiring the possibility of adjustment, both for the effectiveness of the elastic guard and for comfort, a common lacing must be used for joining two opposite edges of an elastic sanitary band or garment so as to allow to control the tautness and/or to modulate it along its length. The adjustment of the tautness by loosening or tightening the lacing is a wearisome and not very practical operation. In order to obviate the laboriousness of a lacing, use is often made of the so-called "Velcro"® wherein a strip material having a population of tiny hooks fasteners is sewn on the surface of an edge of the sanitary protection, garment or footwear and may be pressed into an anchoring engagement on the surface of a cooperating strip of piled fabric. The range of adjustment of the tautness depends obviously upon the size of the area of piled fabric available for anchoring the hooked part of the Velcro, that is either sewn over the opposite edge of the elastic implement or on the same edge thereof, in which case the band of Velcro with the tiny hooks is first passed through a eyelet of the opposite edge of the implement and pulled back to anchor it on the sewn pad of piled fabric. In case Velcro fasteners are used for closing and tightening a substantially tubular sanitary protection or garment, the proper positioning of the sanitary protection around the part of the body to be protected is made difficult by the need of elastically stretching one edge only of the implement before joining the two cooperating parts of the Velcro fastener, often resulting in accidental slippings of the sleeve or bandage, which must be repositioned after fastening it.

When, as it is often the case, these sanitary implements, bandages or garments are wholly or at least partially made of an elastic fabric comprising textile yarn of a natural or synthetic fiber, interwoven by knitting or other suitable weaving techniques with elastomeric yarns so as to produce an elastic fabric, paddings of a suitable fabric (pile) must be applied in the areas where the hooked Velcro material, sewn in proximity of a superimposable edge of the elastic fabric may be anchored. This need to provide for suitable Velcro anchoring pads arises from the fact that the elastic fabric cannot withstand repeated engagements with the tiny hooks of the Velcro material, which would quickly and irremediably damage the elastic fabric.

On the other hand, the need to have Velcro anchoring pads of a suitable pile sewn on the outer surface of the elastic implement implies the presence of local bumps and stiffenings which may have wearisome outcomes, especially in case of prolonged use of these implements for dynamic activities.

Furthermore, a predefined position of these anchoring pads Velcro limits the possibility to adjust tautness of the garment or sanitary protection and retail shops of these implements must keep an adequate stock of different sizes.

When, as it often occurs, the sanitary implement comprise stiffeners or reinforcements permanently or removably inserted into dedicated pockets or housings, the ability of an elastic bandage of a certain size to fit different situations (sizes) is even more reduced, in spite of an ability to stretch. In fact, the requirement of properly positioning of such stiffeners or supports with respect to the articulation or limb to be supported or immobilized practically makes the implement hardly suitable to fit body conformations or even marginally different sizes, thus forcing, especially in these cases, to keep a large stock of close sizes.

The keeping of large stocks of differently sized articles has a precise cost in terms of working capital tied up, which is especially critical for specialized commercial enterprises with a relatively small volume of business.

In a prior patent application PCT/IT98/00054 filed on Mar. 17, 1998, and claiming the priority of Italian Patent Application No. VA/97/A0012 filed on Apr. 16, 1997, a special elastic fabric directly engageable by Velcro fasteners and a number of sanitary protection implements made with such a special elastic material having normal unlimited ability to fit people of different body sizes are described. In particular, an elastic waistband having one end in the form of two independently stretchable and anchorable triangular tail portions is described (FIGS. 4–5).

In the document PCT/IT98100055 filed on Mar. 17, 1998, and claiming the priority of Italian Patent Application No. VA/97/A/0006 filed on Mar. 18, 1997, a tightening and elastic tautness adjustment device for a garment of sanitary protection or alike implement to be tightly worn, is described. The article is composed of at least a first elastic textile band formed of a plurality of parallel elastic strips (2) extending from a first edge of the garment or sanitary protection and having their free ends sewn onto a first strip (8) of hooked Velcro material and at least a second elastic textile band similarly formed of a plurality of parallel elastic strips (2') extending from a second edge of the garment or sanitary protection opposed to the first edge, and interlaced with the parallel strips (2) of the first band, their free ends being sewn onto a second strip of hooked Velcro material.

The mutually interlaced multistrip elastic bands are stretchable by pulling apart the two Velcro strips to be eventually anchored on the outer surface of the implement in the desired position.

For certain affections and application, the elastic tautness of a sanitary implement is not a sufficient condition of effectiveness and the implement must include stiffening members for exerting a proper supporting action. This is the case of a waistband for providing an adequate support of the trunk in case of deviar lumbar affections and during recovery periods from spinal surgeries and so forth.

In cases like these, it is even more important to ensure a perfect fit of the implement and a correct disposition and orientation of the stiffening inserts of the waistband. The known implements tough having a limited ability to be adjusted so as to best fit the waist size of the wearer, they achieve this by a wealth of lacings, Velcro fasteners of difficulty manageability by the wearer itself, which often requires the help of someone else to properly put on the implement in an effective way.

OBJECT AND SUMMARY OF THE INVENTION

It is the main object of the present invention to provide an elastic waistband provided with stiffeners and tautness adjusting means having a structure and a configuration that beside ensuring an ability to fit perfectly a practically unlimited range of body sizes is also easily adjusted by the wearer itself through simple actions while ensuring, in any situation of adjustment, a most appropriate disposition and orientation of the stiffening inserts present in the waistband.

Fundamentally, the waistband of the invention has primary multiple elastic tautness adjusting means and secondary multiple elastic tautness adjusting means, the coordinated adjustment of which provides for an effective correction of the disposition and orientation of the transverse stiffeners incorporated in the elastic waistband.

The distinct adjusting means are easily maneuvered by the wearer without requiring the help of anybody else and may readily be modified to ease or to increase the tautness in function of the postures assumed during the normal activity of the wearer.

Essentially, the elastic waistband of the invention comprises an elastic portion that is composed of a first central portion made of a fabric of greater elasticity and of two side portions made of a fabric of lesser elasticity, a first end portion in the form of two triangle-shaped tails having Velcro fasteners at their free ends and a second end portion having anchoring felt pads on its outer surface.

Transverse stiffening inserts (S1, S2, S3, S4) are disposed in correspondence of the transverse sewing lines joining together the central portion, the two said side portions and the two end portions.

The waistband includes secondary elastic tautness adjustment means, running over the exterior of the three elastic portions and of the inserts, in the form of a plurality of pairs of interlaced multistrip bands, which are spacingly arranged along the height of the waistband. Each multistrip band is composed of a plurality of parallel textile strips having their free ends joined together to a piece of Velcro fastener material and the other ends permanently sewn along the farthest one from said free ends of the transverse sewing lines joining the first central portion of elastic fabric to a respective side portion of stiffer elastic fabric.

The primary tautness adjusting means represented by the two tails, the free end of which is independently pullable and anchorable by way of the Velcro fastener functionally provided thereat, provide for an easy primary adjustment of the tautness of the waistband, enhanced by the possibility of differentiating the tautness between the lower portion (below the waistline) and the upper portion (above the waistline) according to need.

During this preliminary positioning of the elastic waistband, the differentiable tensioning permits also to adjust the position assumed by the transverse stiffeners incorporated in the waistband in a most appropriate way along the circumference of the waistband and also partly determine a certain slanting of the otherwise vertical orientation of the stiffeners, in order to best fit the body of the wearer.

The multiple secondary elastic tautness adjusting means in the form of a plurality of pairs of interlaced multistrip bands, apart from permitting a precise trimming of the fit of the waistband because of the ability of modifying the relative stretching between the central elastic portion of the band and one and/or the other of the two side elastic portions, by externally embracing the whole elastic portion of the band and the stiffeners incorporated therein, they determine a firm blocking in the assumed position and orientation of the stiffeners, which may thus exert a most effective and unyielding supporting action.

BRIEF DESCRIPTION OF THE DRAWINGS

The various features and advantages of the waistband of the invention will be even more clearly recognized through the following description of a sample implementation and by referring to the attached drawings, wherein.

Figure 5:
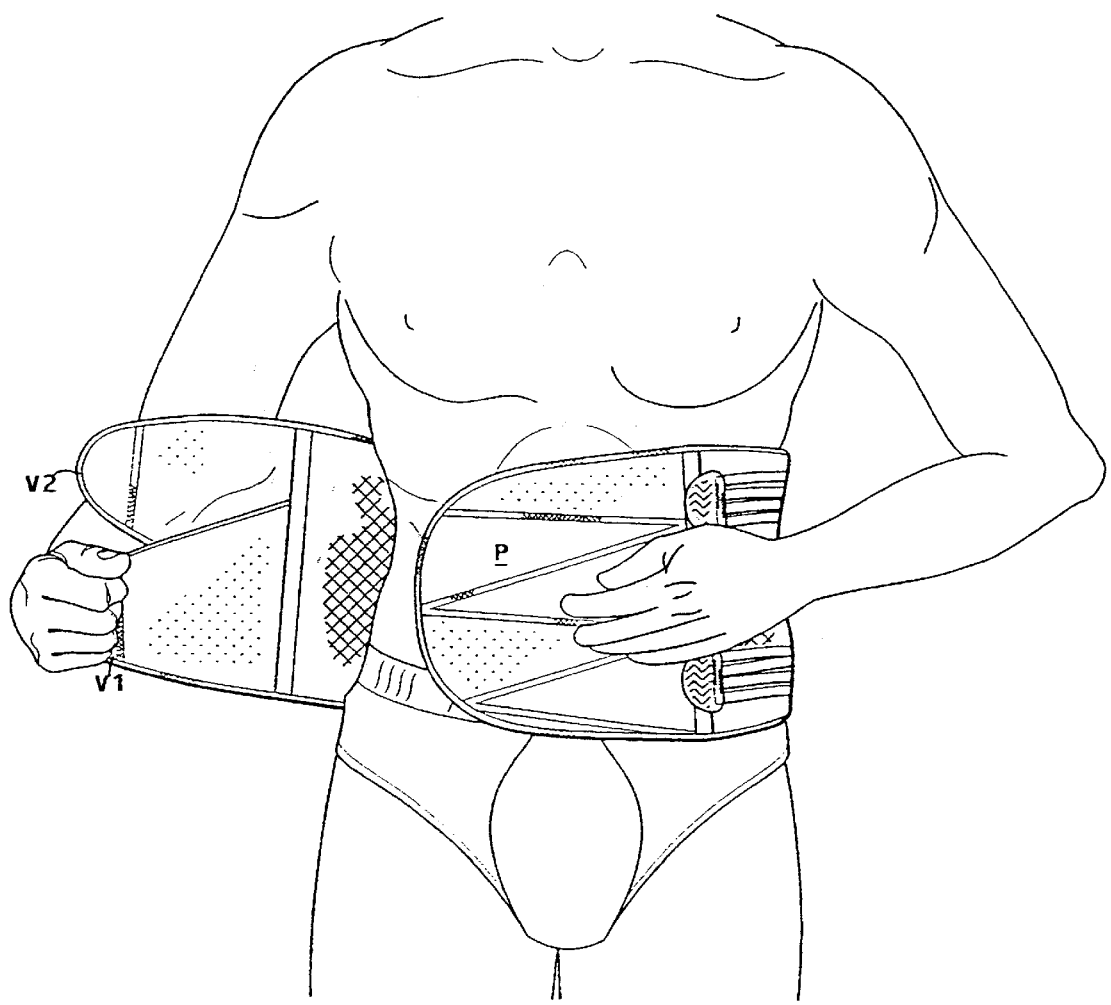
Figure 6:
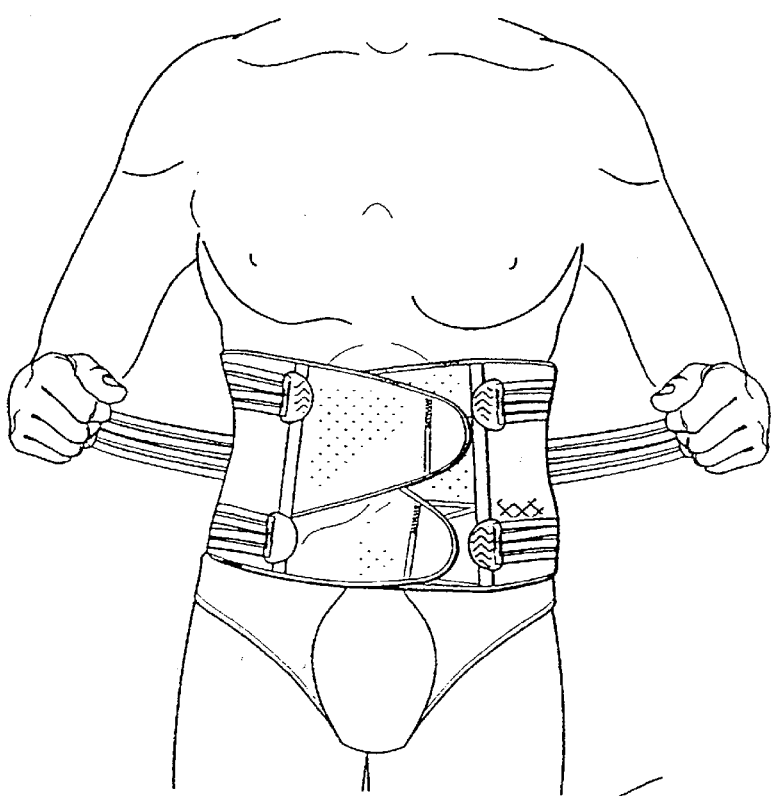
Figure 7:
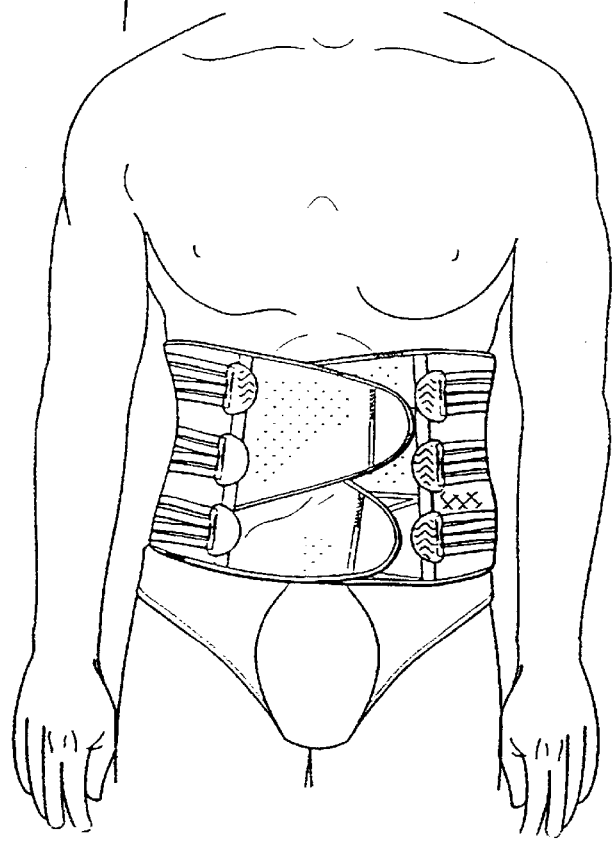

the series of FIGS. 5 to 7 show how the elastic waistband of the invention may be set in place by simple actions of the wearer himself.

DESCRIPTION OF AN EMBODIMENT OF THE INVENTION

With reference to the figures, wherein the same identifiers are used to identify the same parts, the elastic waistband of the invention comprises a main portion A essentially made of an elastic fabric, a first end portion B in the form of two triangle-shaped tails P1 and B2 joined together to the main portion A along a transverse sewing line. The free end tip of each portion B2 and B1 is provided with a Velcro fastener V1 and V2.

A second end portion C is joined to the other end of the main elastic portion A and has an outer surface in the form of a felt onto which the Velcro fasteners V1 and V2 of the two tails B1 and B2 may be engaged.

According to an important aspect of the elastic waistband of the invention, the elastic portion A of the waistband is composed of a central portion A1 of an elastic fabric 1 joined by sewing to two side portions A2 and A3 of a different elastic fabric 2 of lesser elasticity than the fabric 1 with which is made the central portion Al. In other words, the elasticity of the fabric used for the central portion Al is more pronounced than the elasticity of the fabric with which the side potions A2 and A3 are made which are somewhat stiffer and stretch less readily than the central portion A1.

In correspondence of the transverse sewing lines the four different portions that make up the waistband, are incorporated into dedicated pockets, suitable transverse stiffeners S1, S2, S3 and S4 that may be in the form of flattened strips of a coiled metal wire or of a plastic material having an enhanced flexibility in a direction of bending normal to the plane of the waistband and a reduced flexibility in a direction of bending laying on the plane of the waistband, according to the common practice.

In the example shown in the figures, the waistband comprises three independently maneuverable secondary tautness adjustment means, in the form of three pairs, 4, 5 and 6, of interlaced multistrip bands disposed along the height (width) of the waistband.

Each multistrip band of each pair is composed of a plurality of parallel textile strips: 4a–4b, 5a–5b, 6a–6b, the free (or current) ends of which are joined together to a piece of a Velcro fastener: V4, V5, V6, while the other (fixed) ends are permanently sewn along the farthest one of the transverse sewing lines (A1–2 and A–3) that join together the central portion A1 of elastic fabric 1 to the respective side portion A2 or end A3 of stiffer elastic fabric 2.

Figure 1:
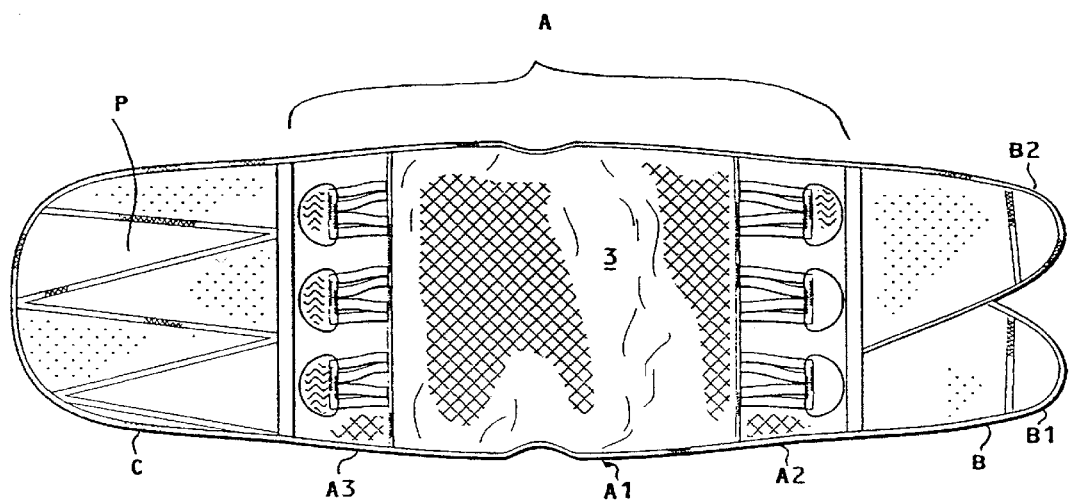
FIG. 1 is a view of the external face of the waistband of the invention.
Figure 2:
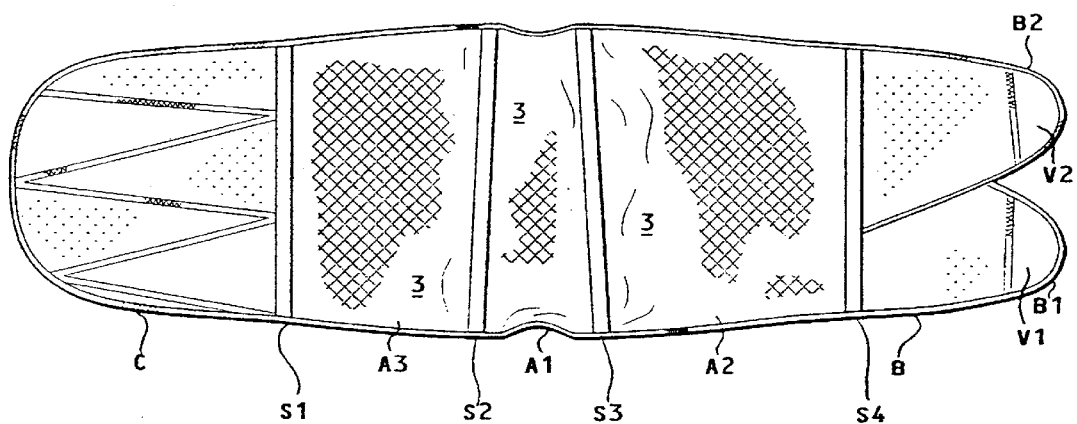
FIG. 2 is a view of the interior face of the waistband of the invention.
Figure 4:
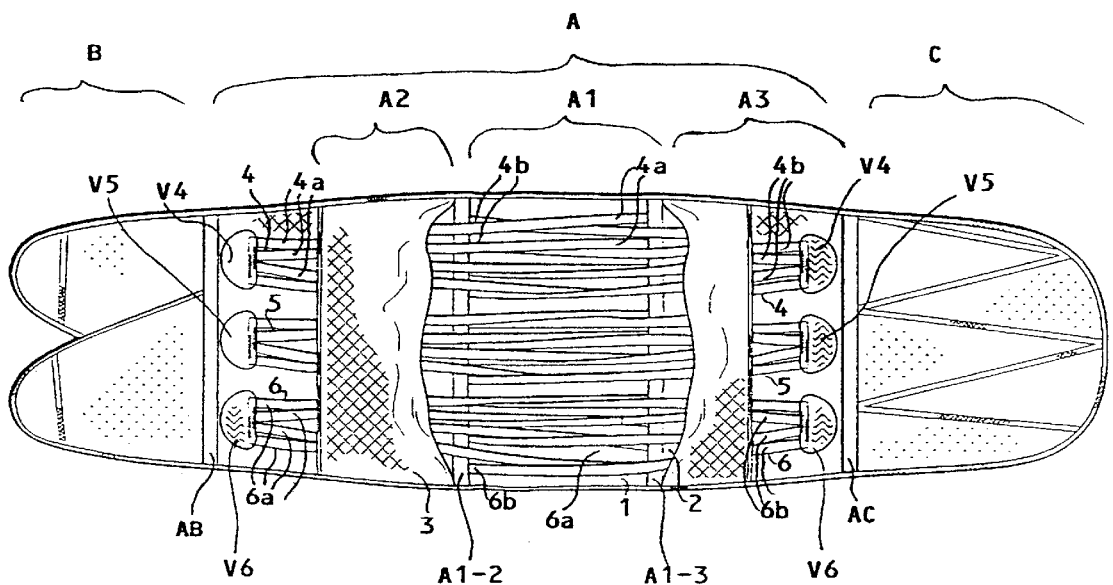
FIGS. 3 and 4 are similar to FIGS. 1 and 2 in which an elastic textile covering panel has been broken open to reveal the inner structure of the waistband.
Figure 3:
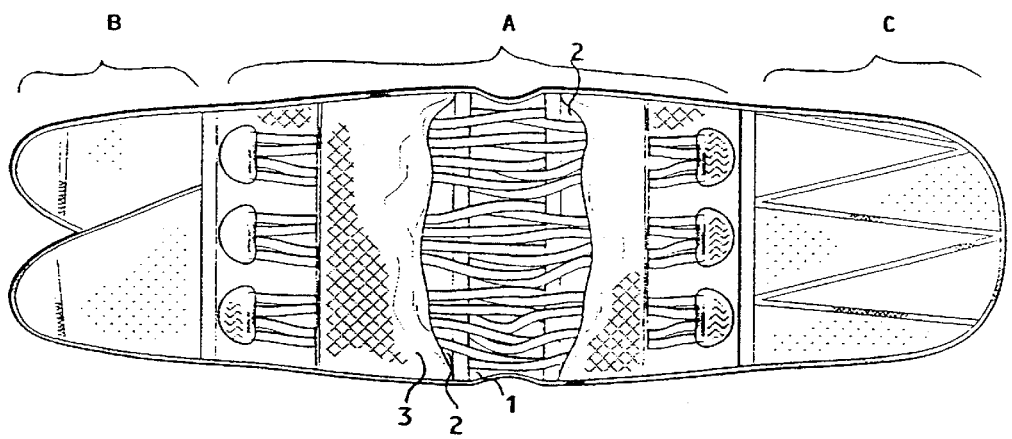

As visible in the partly cutout view of FIGS. 3 and 4, the textile strips run over the exterior of the elastic portions A1, A2 and A3 of the waistband and functionally embrace the transverse stiffening inserts. A covering panel 3 of a light elastically stretchable fabric is sewn at spaced points upon its transverse edges and maintain an orderly disposition of the secondary elastic tautness adjustment interlaced multistrip bands.

At rest, the Velcro pieces V4, V5, V6 may be anchored at rest on the exterior surface of the side portions A2 and A3 for an orderly storage of the waistband.

As pictorially depicted in FIGS. 5, 6 and 7, the waistband is worn around the waistline and preliminarily one or the other of the two triangle-shaped tails is fixed by anchoring its Velcro fastener V1 or V2 over the felt padded exterior face of the end portion C of the waistband. The other tale end may then be pulled and anchored in a similar fashion. The wearer may repeatedly adjust the tautness of the upper portion of the waistband and of the lower portion of the waistband by finding a most appropriate anchoring position for the two triangle-shaped tails.

In this process, the relative position and orientation of the transverse stiffening inserts S1, S2, S3 and S4 is also adjusted to best fit the waist of wearer.

Subsequently, the secondary elastic tautness adjustment means in the form of the three distinct interlaced multistrip bands 4, 5 and 6 are maneuvered by the wearer in succession as depicted in FIG. 6.

By repeated maneuvers, the wearer is able to precisely correct the relative position along the circumference of the waistband of the transverse stiffeners and to block them more or less tightly in position, even by pulling apart the two opposite ends of, an interlaced multistrip band and anchoring the respective velcro fasteners V4, V5 and V6 in a most appropriate position on the outer felt padded surface of the end portions c and eventually also of the two tails B1 and B2.

What is claimed is:

1. An elastic waistband comprising:

at least a main portion made of an elastic fabric, a first end portion in the form of two triangle-shaped tails joined together to said main portion and having at their free ends hook and loop fasteners and a second end portion having anchoring felt pads for said hook and loop fasteners, said elastic main portion being composed of a first central portion of a fabric having a greater elasticity than an elasticity of a fabric of two side portions each joined with said central portion along an associated one of a plurality of transverse sewing lines;

transverse stiffening inserts each being disposed in correspondence with one of said plurality of transverse sewing lines joining together said first central portion, said side portions and said first and second end portions;

secondary elastic tautness adjustment means running over an exterior of said elastic portions and of said inserts and being in the form of a plurality of pairs of interlaced multistrip bands spacingly arranged along a height of the waistband, each multistrip band being composed of a plurality of parallel textile strips each having a free end thereof joined with a piece of hook and loop fastener material, and opposing ends of each of said plurality of parallel textile strips being sewn along a most distant one of said plurality of transverse sewing lines from said free ends of said transverse sewing lines to join said first central portion of elastic fabric to a respective side portion of the stiffer elastic fabric of said two side portions;

hook and loop fasteners of the opposite free ends of each pair of interlaced bands being pullable apart and anchorable on an outer surface of said first and second end portions, respectively, for adjusting a relative stretching of said elastic portions and for positioning said stiffeners.

2. The elastic waistband of claim 1, further comprising an external panel of elastic fabric partially covering said secondary elastic tautness adjustment means, and having edges sewn at intervals to the underlying side portion to retain, in an orderly and spaced disposition, the free ends of said interlaced multistrip bands extending outside of said edges.

* * * * *